(12) United States Patent
Han et al.

(10) Patent No.: US 10,330,682 B2
(45) Date of Patent: Jun. 25, 2019

(54) COMPOSITION FOR DIAGNOSING PANCREATIC CANCER AND METHOD FOR DIAGNOSING PANCREATIC CANCER USING SAME

(71) Applicants: SK TELECOM CO., LTD., Seoul (KR); Seoul National University R&DB Foundation, Seoul (KR)

(72) Inventors: Sangjo Han, Seoul (KR); Yonghwan Choi, Seoul (KR); Sung Gon Yi, Seoul (KR); Taegyun Yun, Seoul (KR); Junghyun Namkung, Seoul (KR); Youngsoo Kim, Seoul (KR); Taesung Park, Seoul (KR); Jin-Young Jang, Seoul (KR)

(73) Assignees: SK TELECOM CO., LTD., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 14/901,157

(22) PCT Filed: Oct. 31, 2014

(86) PCT No.: PCT/KR2014/010354
§ 371 (c)(1),
(2) Date: Dec. 28, 2015

(87) PCT Pub. No.: WO2015/065097
PCT Pub. Date: May 7, 2015

(65) Prior Publication Data
US 2016/0252512 A1    Sep. 1, 2016

(30) Foreign Application Priority Data

Oct. 31, 2013 (KR) .................. 10-2013-0131150
Oct. 31, 2013 (KR) .................. 10-2013-0131248

(51) Int. Cl.
*G01N 33/574* (2006.01)
*C12Q 1/6886* (2018.01)
*C12Q 1/68* (2018.01)

(52) U.S. Cl.
CPC ..... *G01N 33/57438* (2013.01); *C12Q 1/6886* (2013.01); *C12Q 2600/158* (2013.01); *G01N 2333/705* (2013.01); *G01N 2333/91188* (2013.01); *G01N 2333/924* (2013.01)

(58) Field of Classification Search
None
See application file for complete search history.

(56) References Cited

U.S. PATENT DOCUMENTS

| | | | | |
|---|---|---|---|---|
| 7,939,263 | B2 * | 5/2011 | Clarke | ................ C12N 5/0693 435/6.12 |
| 9,572,874 | B2 * | 2/2017 | Fotin-Mleczek | .......................... A61K 39/0011 |
| 9,616,084 | B2 * | 4/2017 | Mutzke | ................ C12N 15/87 |
| 2010/0190686 | A1 | 7/2010 | Wells | |
| 2011/0294136 | A1 | 12/2011 | Meyer | |
| 2012/0040861 | A1 | 2/2012 | Williams | |
| 2012/0295803 | A1 | 11/2012 | Beer | |

FOREIGN PATENT DOCUMENTS

| | | |
|---|---|---|
| CN | 103033619 | 4/2013 |
| EP | 2366800 | 9/2011 |
| KR | 10-2007-0119250 | 12/2007 |
| KR | 10-0819122 | 3/2008 |
| KR | 10-2009-0003308 | 1/2009 |
| KR | 10-2012-0009781 | 2/2012 |
| KR | 10-2012-0082372 | 7/2012 |
| WO | 2008/077165 | 7/2008 |
| WO | 2012/158780 | 11/2012 |

OTHER PUBLICATIONS

In Keun Choi, et al., "High serum YKL-40 is a poor prognostic marker in patients with advanced non-small cell lung cancer", Acta Oncologica, Vo. 49, No. 6, pp. 861-864, Jun. 16, 2010.
Search Report, State Intellectual Property Office of the P.R.C, Application No. 2014800427382, dated Sep. 19, 2016.
Li Wenbo, "Biomarker Prediction for Pancreatic Cancer and Liver Cancer Based on Microarray", Chinese Master Theses Full-text Database Medicine and Health Sciences, No. 10, Abstract, p. 27-44 of the text, Oct. 15, 2012.
C. Haglund et al., "Evaluation of CA19-9 as a serum tumor marker in pancreatic cancer", Br. J. Cancer, vol. 53, p. 197-202, Dec. 31, 1986.
Nicolai A. Schultz et al., "Diagnostic and Prognostic Impact of Circulating YKL-40, IL-6,and CA 19.9 in Patients with Pancreatic Cancer", PLOS ONE, vol. 8, No. 6, p. 1-9, Jun. 30, 2013.
SIPO, Search Report of CN 201480042738.2 dated Jun. 2, 2017.

* cited by examiner

*Primary Examiner* — Antonio Galisteo Gonzalez
(74) *Attorney, Agent, or Firm* — Lex IP Meister, PLLC

(57) ABSTRACT

A composition, for diagnosing the possibility of onset of pancreatic cancer including an agent measuring the expression level of marker protein of diagnosing the possibility of onset of pancreatic cancer, or mRNA expression level of a gene encoding the protein, a kit including the composition, and a method of diagnosing pancreatic cancer using the maker are provided. The diagnostic markers of pancreatic cancer in accordance with the present disclosure are useful for predicting or diagnosing the onset, the possibility of onset, and the severity of pancreatic cancer in an early stage, and are also applied to a study on the tumorigenesis of pancreatic cancer. In addition, the diagnosis method of the present invention allows for the convenient detection of pancreatic cancer in a non-invasive manner in a sample such as blood.

8 Claims, 11 Drawing Sheets

Specification includes a Sequence Listing.

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: internal standard beta-galatosidase peptide

<400> SEQUENCE: 1

Gly Asp Phe Gln Phe Asn Ile Ser Arg
1               5
```

COMPOSITION FOR DIAGNOSING PANCREATIC CANCER AND METHOD FOR DIAGNOSING PANCREATIC CANCER USING SAME

TECHNICAL FIELD

The present disclosure relates to a composition and a kit for diagnosing pancreatic cancer, comprising an agent for measuring a protein expression level of a protein or a mRNA expression level of a gene encoding the protein being available for determining the onset or the possibility of onset of pancreatic cancer, and a method for the diagnosis of pancreatic cancer using the composition or the kit.

BACKGROUND ART

Representative among main diseases of people these days is cancer. Studies on cancer are actively ongoing, particularly in the areas of high-prevalence cancers including lung cancer, liver cancer, stomach cancer, etc., but there are fewer studies being conducted on low-prevalence cancers including esophageal cancer, colorectal cancer, pancreatic cancer, etc.

In particular, pancreatic cancer usually does not cause recognizable symptoms in its early stages, and the disease is typically not diagnosed due to its minor symptoms such as pain, weight loss, etc., until it has spread beyond the pancreas itself to the whole body. Moreover, pancreatic cancer is generally poor in survival rate, and thus periodical diagnosis is very important. Clinical symptoms of pancreatic cancer are, in most part, slowly exposed, and patients with pancreatic cancer most commonly suffer from feebleness, anorexia, and weight loss. Found to have a five-year survival rate of 1-4% with a median survival time of 5 months, pancreatic cancer is very fatal and is the poorest in prognosis among human cancers. After diagnosis, it is found that 80-90% of people are impossible to treat by hopeful curative resection. This is one of the main reasons for the generally highly poor prognosis. Pancreatic cancer is predominantly treated with chemotherapy. Therefore, in comparison to other cancers, there is a desperate need for an early diagnosis method of pancreatic cancer. Although known so far to be useful in treating pancreatic cancer, several anticancer agents including 5-fluorouracil, gemcitabine, and tarceva, exhibit very low curative effects and a reaction rate of only around 15% for cancer treatment. These situations suggest there is a pressing request for more effective early diagnosis and therapy for pancreatic cancer whereby the prognosis can be improved.

Diagnosis of pancreatic cancer is determined upon hematologic examination (CA19-9), gastrointestinography and duodenography with X-ray contrast media, cholangiography through the skin and the liver, or endoscopic retrograde cholangiopancreatography. Many disease lesions can be detected by such methods, but currently, ultrasonography and computed tomography are the most preferred. More deliberate biopsy methods might result in relatively more accurate outcomes. The diagnosis methods described above are used because they are generally accurate; however, subjects are unwilling to undergo examination because such diagnosis methods are uncomfortable or painful. Hence, there is need for method of diagnosing pancreatic cancer conveniently and rapidly.

In this context, Korean Patent No. 10-0819122 discloses technologies using various pancreas cancer markers including matrilin, transthyretin, and stratifin. In addition, Korean Patent Unexamined Application Publication No. 2012-0082373 describes the diagnosis of pancreatic cancer by using various makers for pancreatic cancer. KR2009-0003308 discloses diagnosis of pancreatic cancer through the detection of an expression level of REG4 in a blood sample from a subject. KR 2012-0009781A describes an analysis method for measuring an XIST RNA expression level in a cancer tissue from a subject, whereby information on the onset of pancreatic cancer in the subject can be provided. KR2007-0119250A discloses a family of new LBFL313 genes that are expressed in different patterns between normal pancreatic tissues and pancreatic cancer tissues. US 2011/0294136A1 discloses a diagnosis method of pancreatic cancer using biomarkers including keratin 8 protein. However, diagnostic efficiency and accuracy greatly differ from one marker to another. Therefore, there is a pressing need for an excellently efficient marker and a diagnosis method using the same.

The present inventors had made an effort to develop a maker being useful for diagnosing a pancreatic cancer in an early stage, and thus identified proteins over-expressed or under-expressed in pancreatic cancer, and completed the present invention by confirming that the pancreatic cancer could be easily diagnosed with the proteins.

DISCLOSURE

Technical Problem

Therefore, it is an object of the present disclosure to provide a diagnostic composition of pancreatic cancer with which the possibility of onset of pancreatic cancer can be conveniently diagnosed in an early stage.

It is a further object of the present disclosure to provide a kit for diagnosing pancreatic cancer, comprising the composition.

It is a still further object of the present disclosure to provide a method for diagnosing pancreatic cancer or for providing information on a diagnosis result of pancreatic cancer, using the diagnosis composition or kit.

Technical Solution

To accomplish the above objects, the present disclosure provides a composition for diagnosing pancreatic cancer, comprising an agent for measuring protein expression level of ABAT protein (4-aminobutyrate aminotransferase; GenBank Accession No: NP_001120920.1) or mRNA expression level of a gene encoding ABAT protein.

To accomplish the above objects, the present disclosure provides a composition for diagnosing pancreatic cancer, comprising an agent for measuring protein expression level of ABAT protein (4-aminobutyrate aminotransferase; GenBank Accession No: NP_001120920.1) or mRNA expression level of a gene encoding ABAT protein; and expression level of CHI3L1 protein (Chitinase-3-like protein 1 precursor; GenBank Accession No: NP_001267.2) or mRNA expression level of a gene encoding CHI3L1 protein.

To accomplish the above objects, the present disclosure provides a kit for diagnosing pancreatic cancer, comprising the composition.

To accomplish the above objects, the present disclosure provides a method for diagnosing pancreatic cancer, comprising:

(a) obtaining a sample from a subject to be diagnosed for the onset of pancreatic cancer;

(b) measuring protein expression level of ABAT protein (4-aminobutyrate aminotransferase; GenBank Accession No: NP_001120920.1) or mRNA expression level of a gene encoding ABAT protein;

(c) comparing the protein expression level of ABAT protein or mRNA expression level of a gene encoding ABAT, with those of corresponding normal control; and (d) determining that the onset or the possibility of onset of pancreatic cancer is high, when the protein expression level of ABAT protein or mRNA expression level of a gene encoding ABAT protein in the subject to be detected for onset of pancreatic cancer is higher than those of corresponding normal control for onset of pancreatic cancer, based on the comparison result in (c) step.

To accomplish the above objects, the present disclosure provides a method for diagnosing pancreatic cancer, comprising:

(a) obtaining a sample from a subject to be diagnosed for the onset of pancreatic cancer;

(b) measuring protein expression level of ABAT protein (4-aminobutyrate aminotransferase; GenBank Accession No: NP_001120920.1) or mRNA expression level of a gene encoding ABAT protein, and protein expression level of CHI3L1 protein (Chitinase-3-like protein 1 precursor; GenBank Accession No: NP_001267.2) or mRNA expression level of a gene encoding CHI3L1 protein;

(c) comparing the protein expression level of ABAT protein or mRNA expression level of a gene encoding ABAT protein and the protein expression level of CHI3L1 protein or mRNA expression level of a gene encoding CHI3L1 protein, with those of corresponding normal control; and (d) determining that the onset or the possibility of onset of pancreatic cancer is high, when the protein expression level of ABAT protein or mRNA expression level of a gene encoding ABAT protein in the subject to be detected for onset of pancreatic cancer is higher than those of corresponding normal control, and when the protein expression level of CHI3L1 protein or mRNA expression level of a gene encoding CHI3L1 protein in the subject to be detected for onset of pancreatic cancer is lower than those of corresponding normal control in the subject, based on the comparison result in (c) step.

The marker of diagnosing a pancreatic cancer in accordance with the present invention can make it possible to significantly estimate or determine the possibility of onset of the pancreatic cancer, to diagnose the pancreatic cancer in an early stage and the severity degree of pancreatic cancer. In addition, the diagnosis method of the present invention allows for the convenient detection of pancreatic cancer from a sample such as blood in a non-invasive manner.

Advantageous Effects

As described hitherto, diagnostic markers of pancreatic cancer in accordance with the present disclosure are useful for predicting or diagnosing the onset, the possibility of onset, and the severity of pancreatic cancer in an early stage. The markers are also applied to a study on the tumorigenesis of pancreatic cancer. In addition, the diagnosis method of the present invention allows for the convenient detection of pancreatic cancer in a sample such as blood in a non-invasive manner.

MODE FOR INVENTION

Figure 1:
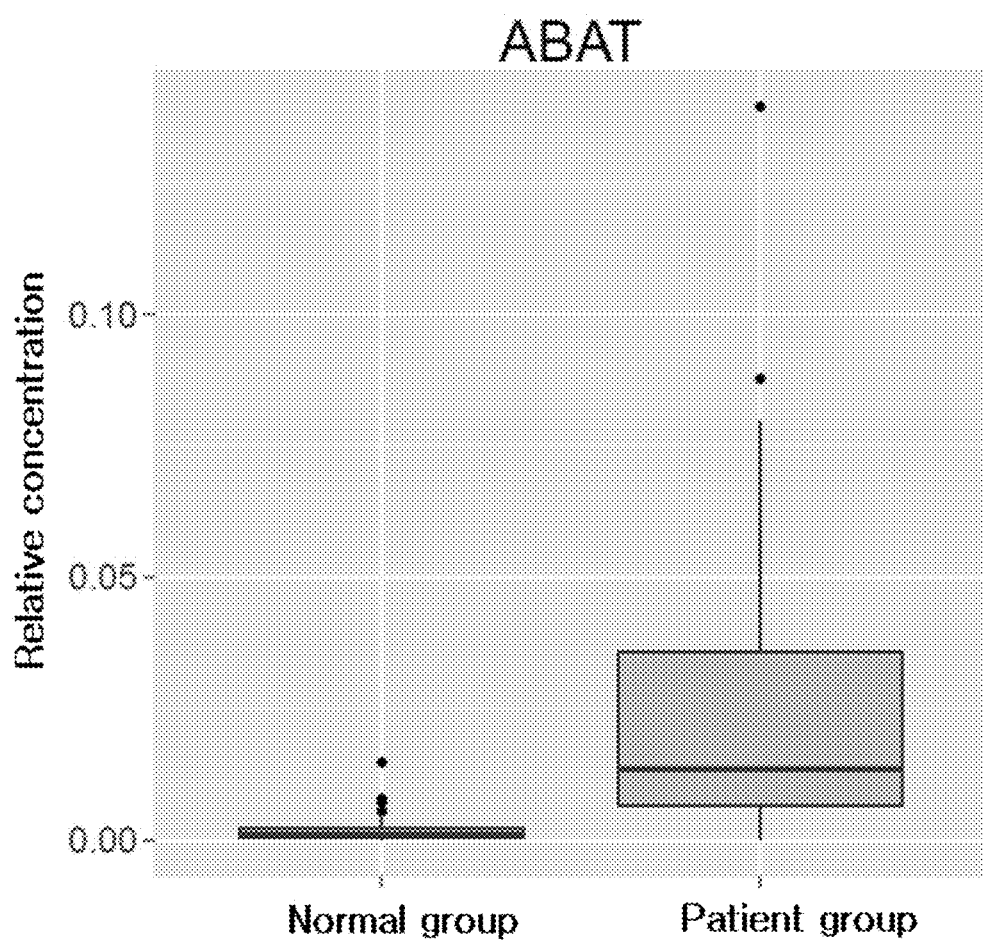
FIG. 1 is a graph showing the relative concentration of ABAT protein in a control and a patient group with pancreatic cancer, as measured by MRM quantitative analysis.

The terms are defined hereinafter.

As used herein, the term "diagnosis" is intended to encompass determining the susceptibility of a subject to a certain disease or disorder, determining whether a subject is affected with a certain or disorder, determining the prognosis of a subject affected with a certain or disorder (e.g., identifying pre-metastatic or metastatic states of cancer, determining cancer stages or the responsiveness of cancer to treatment), or therametrics (e.g., monitoring the state of a subject to provide information on therapeutic efficacy). Particularly, the diagnosis, as used herein, means the determination of the onset or the possibility of onset (risk) of pancreatic cancer.

The term "pancreatic cancer", as used herein, means cancer (carcinoma) or malignant tumors that arise from cells in the pancreas. There are various kinds of pancreatic tumors and 90% of such tumors are pancreatic ductal adenocarcinomas (PDAC). Thus, pancreatic ductal adenocarcinoma is referred to, in a narrow sense, as pancreatic cancer. Other examples of pancreatic cancer include neuroendocrine tumors and cystadenocarcinoma.

The term "marker", "biomarker", or "diagnostic marker", as used herein, means a label that allows for discrimination between normal and ill states or which enables therapeutic outputs to be predicted or objectively measured. In particular, in the context of relevance to pancreatic cancer, a marker means an organic biomolecule, such as a polypeptide or nucleic acid (e.g., mRNA, etc.), a lipid, a glycolipid, a glycoprotein, a sugar (monosaccharide, disaccharide, oligosaccharide, and the like), etc., which significantly increases or decreases in protein or gene expression level in a subject with pancreatic cancer or at risk of the onset of pancreatic cancer, compared to a normal control (subjects without pancreatic cancer).

The present disclosure provides a composition for diagnosing pancreatic cancer, comprising an agent for measuring protein expression level of ABAT protein (4-aminobutyrate aminotransferase; GenBank Accession No: NP_001120920.1) or mRNA expression level of a gene encoding ABAT protein.

In the present invention, ABAT is used as a marker for detecting pancreatic cancer, thereby effectively diagnosing the onset of the possibility of onset of pancreatic cancer in a subject.

ABAT (4-aminobutyrate aminotransferase) used as a marker for detecting pancreatic cancer is also called as GABA transaminase or 4-aminobutyrate transaminase, and is involved in the decomposition of GABA as a nerve suppressive material in a central nerve system into succinic semialdehyde. The ABAT is homo-dimer comprised of 50 kD subunits which forms a complex with pyridoxal-5-phosphate. The deficiency of ABAT causes the symptoms such as mental retardation, muscle weakness, hyperreflexia, lethargic, refractory seizure, and problem with brain wave. However, ABAT has not been known as a marker for detecting a pancreatic cancer as yet.

The present inventors confirms that ABAT is used as a marker for detecting pancreatic cancer, thereby effectively diagnosing the onset or the possibility of onset of pancreatic cancer in a subject at high sensitivity and reliability. Particularly, the present inventors analyzed the serum samples from the subjects with pancreatic ductal adenocarcinomas (PDAC), intraductal papillary mucinous neoplasm (IPMN) and chronic cholecystitis, identified ABAT as a biomarker overexpressed in a pancreatic cancer, and proved the effective biomarker of pancreatic cancer by analyzing the serum sample from a normal subject with other than pancreatic cancer.

The present disclosure provides a composition for diagnosing pancreatic cancer, comprising an agent for measuring protein expression level of ABAT protein (4-aminobutyrate aminotransferase; GenBank Accession No: NP_001120920.1) or mRNA expression level of a gene encoding ABAT protein, and protein expression level of CHI3L1 protein (Chitinase-3-like protein 1 precursor; GenBank Accession No: NP_001267.2) or mRNA expression level of a gene encoding CHI3L1 protein.

In the present invention, the combination of ABAT and CHI3L1 is used as a marker for detecting pancreatic cancer, thereby effectively diagnosing the onset or the possibility of onset of pancreatic cancer in a subject.

In the composition for diagnosing pancreatic cancer using the combination of ABAT and CHI3L1, ABAT is the same as described above. CHI3L1 (Chitinase-3-1 like protein 1 precursor; GenBank Accession No: NP_001267.2) used as a marker for detecting pancreatic cancer is also called as Cartilage glycoprotein 39 and belongs to glycosyl hydrolase 18 family. The ABAT is homo-dimer comprised of 50 kD subunits which forms a complex with pyridoxal-5-phosphate. CHI3L1 is a kind of glycoprotein secreted to outside of cell, and its expression increases breast cancer, colon cancer, prostatic cancer, ovarian cancer, thyroid carcinoma, lung cancer, liver cancer and the like. However, the combination of ABAT and CHI3L1 has not been known as a marker for detecting a pancreatic cancer as yet.

The present inventors confirms that the combination of ABAT and CHI3L1 is used as a marker for detecting pancreatic cancer, thereby effectively diagnosing the onset or the possibility of onset pancreatic cancer in a subject at high sensitivity and reliability. Particularly, the present inventors analyzed the serum samples from the subjects with pancreatic ductal adenocarcinomas (PDAC), intraductal papillary mucinous neoplasm (IPMN) and chronic cholecystitis identified ABAT as a biomarker overexpressed and CHI3L1 as a biomarker under-expressed in a pancreatic cancer, and proved the effective biomarker of pancreatic cancer by analyzing the serum sample from a normal subject with other than pancreatic cancer.

As used herein, the term "measuring a protein expression level" in the context of pancreatic cancer means detecting and identifying the presence and expression level of a diagnostic marker (protein) for pancreatic cancer or a gene coding therefor in a biological sample. Examples of methods for use in measuring or comparatively analyzing the protein includes, but are not limited to, protein chip assay, immunoassay, ligand binding assay, MALDI-TOF (Matrix Assisted Laser Desorption/Ionization Time of Flight Mass Spectrometry), SELDI-TOF (Surface Enhanced Laser Desorption/Ionization Time of Flight Mass Spectrometry), radioimmunoassay, radial immunodiffusion, Ouchterlony immunodiffusion, Rocket immunoelectrophoresis, immunohistostaining, complement fixation test, 2-D electrophoresis, liquid chromatography-mass spectrometry (LC-MS), liquid chromatography-mass spectrometry/mass spectrometry (LC-MS/MS), Western blotting, and ELISA (enzyme-linked immunosorbentassay).

In the composition for diagnosing pancreatic cancer in accordance with the present disclosure, an agent for measuring a protein expression level of ABAT or CHI3L1 may comprise an antibody, an oligopeptide, a ligand, a PNA (peptide nucleic acid) or an aptamer that can specifically bind to the protein ABAT or CHI3L1.

As used herein, the term "antibody" refers to a substance that specifically binds to an antigen to provoke an antigen-antibody reaction. For the purpose of the present disclosure, the term "antibody" means an antibody that specifically binds to the proteins of ABAT or CHI3L1. Falling within the scope of the antibody of the present disclosure are polyclonal antibodies, monoclonal antibodies, and recombinant antibodies. These antibodies can be easily prepared using a technique well known in the art. In addition, the antibody useful in the present disclosure may be a complete antibody consisting of two full-length light chains and two full-length heavy chains, or a functional fragment of a complete antibody molecule. The term "functional fragment" of an antibody molecule means a fragment retaining an antigen-binding function, as exemplified by Fab, F(ab'), F(ab')$_2$, and Fv.

As used herein, the term "PNA (Peptide Nucleic Acid)" refers to an artificially synthesized polymer similar to DNA or RNA, first introduced by professors Nielsen, Egholm, Berg, and Buchardt (Univ. Copenhagen, Denmark) in 1991. DNA has a phosphoric acid-ribose sugar backbone whereas PNA's backbone is composed of repeating N-(2-aminoethyl)-glycine units linked by peptide bonds. Thanks to this structure, PNA significantly increases in binding affinity and stability for DNA or RNA, and thus is effectively used in molecular biology studies, diagnosis, and antisense therapy. For details of PNA, reference may be made to the document [Nielsen P E, Egholm M, Berg R H, Buchardt O (December 1991). "Sequence-selective recognition of DNA by strand displacement with a thymine-substituted polyamide". *Science* 254 (5037): 1497-1500].

As used herein, "aptamers" are oligonucleotide or peptide molecules that bind to a specific target molecule. With regard to details of aptamers, reference may be made to documents [Bock L C et al., Nature 355(6360):5646(1992); Hoppe-Seyler F, Butz K "Peptide aptamers: powerful new tools for molecular medicine". J Mol Med. 78(8):42630 (2000); Cohen B A, Colas P, Brent R. "An artificial cell-cycle inhibitor isolated from a combinatorial library". Proc Natl Acad Sci USA. 95(24): 142727(1998)].

The term "measuring an mRNA expression level", as used herein, in the context of pancreatic cancer means detecting and identifying the presence and expression level of an mRNA of a gene coding for a diagnostic marker (protein) in a biological sample. Examples of analysis methods available for the measurement of mRNA expression levels in the present disclosure include reverse-transcription polymerase chain reaction (RT-PCR), competitive RT-PCR, real-time RT-PCR, RNase protection assay (RPA), Northern blotting, and DNA chip, but are not limited thereto.

In the composition for diagnosing pancreatic cancer according to the present disclosure, the agent for measuring an mRNA expression level of a gene coding for ABAT and CHI3L1 comprises a primer, probe, or antisense nucleotide that specifically binds to an mRNA of a gene encoding ABAT and CHI3L1. Information on ABAT and CHI3L1 proteins may be obtained from UniProt, and a person skilled in the art can design a primer, probe, or antisense nucleotide that specifically binds to an mRNA of a gene encoding the protein, based on the information.

As used herein, the term "primer" is a strand of short nucleic acid sequences that recognizes target gene sequences, and includes a pair of forward and reverse primers. Particularly, it includes a pair of primers providing analysis results of specificity and sensitivity. A primer is regarded as providing high specificity when it is used to amplify a target gene sequence, but does not cause the amplification of non-target sequences that are inconsistent therewith or complementary thereto.

The term "probe", as used herein, refers to a substance that specifically binds to a target to be detected in a sample. Through the binding, the probe can ascertain the presence of the target in the sample. So long as it is typically used in the art, any probe may be available in the present disclosure. Particularly, the probe may be a PNA (peptide nucleic acid), an LNA (locked nucleic acid), a peptide, a polypeptide, a protein, an RNA, or a DNA, with the most preference for PNA. In detail, the probe is a biomaterial that may be of organism origin or may be synthesized ex vivo, or a mimic thereof. For example, the probe may be an enzyme, a protein, an antibody, a microbe, an animal or plant cell or organ, a neuron, a DNA, or an RNA. The DNA may include cDNA, genomic DNA, and oligonucleotide. Also, within the scope of the RNA, genomic RNA, mRNA, and oligonucleotide may fall. Examples of the protein include an antibody, an antigen, an enzyme, and a peptide.

As used herein, the term "antisense" refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The oligomer may have exact or near sequence complementarity to the target sequence.

In an embodiment, the present invention provides a composition for diagnosing pancreatic cancer, further including an agent for measuring protein expression level of CA19-9 protein (Carbohydrate Antigen 19-9) or mRNA expression level of a gene encoding CA19-9 protein. Specifically, the composition of present invention may include an agent for measuring expression level of ABAT and CA19-9 protein or mRNA expression level of a gene encoding ABAT and CA19-9 protein. In addition, the composition may include the protein expression level of ABAT, CHI3L1 (Chitinase-3-like protein 1 precursor; GenBank Accession No: NP_001267.2) and CA19-9 proteins or mRNA expression level of each gene encoding ABAT, CHI3L1 and CA19-9 proteins.

CA19-9 protein has been known as a maker for pancreatic cancer [Safi F. et al., "Diagnostic importance of the tumor marker CA 19-9 in pancreatic cancer", Dtsch Med Wochenschr 109(49): 1869-73(1984); Wang F M et. al., "The significance of CA19-9 tumor antigen in the serum of patients with carcinomas". Proc Natl Sci Counc Repub China B, April 9(2): 119-25(1985)]. The measurement values of two makers, ABAT and CA19-9 or three markers of ABAT, CHI3L1 and CA19-9 can provide more accurate and effective diagnosis of pancreatic cancer.

Further, the present disclosure provides a kit for diagnosing pancreatic cancer, comprising the composition for the diagnosis of pancreatic cancer. For example, the kit may be an RT-PCR kit, a DNA chip kit, an ELISA kit, a protein chip kit, a rapid kit, or an MRM (multiple reaction monitoring) kit.

For example, the diagnostic kit may further comprise an element necessary for a reverse transcription polymerase chain reaction. A RT-PCR kit comprises a pair of primers specific for a gene encoding a marker protein. Each primer is a nucleotide having a sequence specific for a nucleic acid sequence of the gene, and may have a length of about 7 to 50 bp, and more particularly about 10 to 30 bp. Further, the kit may further comprise a primer specific for a nucleic acid sequence of a control gene. In addition, the RT-PCR kit may comprise a test tube or a suitable vessel, a reaction buffer (various pH values and magnesium concentrations), deoxynucleotides (dNTPs), enzymes such as Taq-polymerase and reverse transcriptase, a DNase inhibitor, an RNase inhibitor, DEPC-water, and sterile water.

Further, the diagnostic kit of the present disclosure may comprise an element necessary for operating a DNA chip. The DNA chip kit may comprise a substrate to which a gene or a cDNA or oligonucleotide corresponding to a fragment thereof is bound, and reagents, agents, and enzymes for constructing a fluorescence-labeled probe. In addition, the substrate may comprise a control gene or a cDNA or oligonucleotide corresponding to a fragment thereof.

In some embodiments, the diagnostic kit of the present disclosure may comprise an element necessary for performing ELISA. The ELISA kit may comprise antibodies specific for the proteins. The antibodies have high selectivity and affinity for the marker proteins, with no cross-reactivity to other proteins, and may be monoclonal antibodies, polyclonal antibodies, or recombinant antibodies. Further, the ELISA kit may comprise an antibody specific for a control protein. In addition, the ELISA kit may further comprise a reagent capable of detecting the bound antibody, for example, a labeled secondary antibody, chromophores, an enzyme (e.g., conjugated with an antibody), and a substrate thereof or an material capable of binding to the antibody.

Moreover, the present invention provides a method for diagnosing pancreatic cancer An embodiment of method for diagnosing pancreatic cancer includes the following steps:

(a) obtaining a sample from a subject to be diagnosed for the onset of pancreatic cancer;

(b) measuring protein expression level of ABAT protein (4-aminobutyrate aminotransferase; GenBank Accession No: NP_001120920.1) or mRNA expression level of a gene encoding ABAT protein;

(c) comparing the protein expression level of ABAT protein or mRNA expression level of a gene encoding ABAT, with those of corresponding normal control; and (d) determining that the onset or the possibility of onset of pancreatic cancer is high, when the expression levels of ABAT protein or mRNA expression level of a gene encoding ABAT protein in the subject to be detected for onset of pancreatic cancer is higher than those of corresponding normal control, based on the comparison result in (c) step.

In another embodiment, the method comprises the following steps:

(a) obtaining a sample from a subject to be diagnosed for the onset of pancreatic cancer;

(b) measuring protein expression level of ABAT protein (4-aminobutyrate aminotransferase; GenBank Accession No: NP_001120920.1) or mRNA expression level of a gene encoding ABAT protein, and protein expression level of CHI3L1 protein (Chitinase-3-like protein 1 precursor; GenBank Accession No: NP_001267.2) or mRNA expression level of a gene encoding CHI3L1 protein;

(c) comparing the protein expression level of ABAT protein or mRNA expression level of a gene encoding ABAT protein and the protein expression level of CHI3L1 protein or mRNA expression level of a gene encoding CHI3L1 protein, with those of corresponding normal control; and (d) determining that the onset or the possibility of onset of pancreatic cancer is high, when the expression levels of ABAT protein or mRNA expression level of a gene encoding ABAT protein in the subject to be detected for onset of pancreatic cancer is higher than those of corresponding normal control, and when the expression levels of CHI3L1 protein or mRNA expression level of a gene encoding CHI3L1 protein in the subject to be detected for onset of pancreatic cancer is lower than those of corresponding normal control, based on the comparison result in (c) step.

The term "sample", as used in conjunction with the method, refers to a biological sample that differs in protein or gene expression level, with the onset of pancreatic cancer, and examples of which include a tissue, a cell, a serum, a plasma, saliva, cerebrospinal fluid, and urine, with preference for blood, serum, or plasma.

Because pancreatic cancer patients increase in the expression level of ABAT protein or in the expression level of mRNAs of genes encoding the proteins, increase in the expression level of ABAT protein or in the expression level of mRNAs of gene encoding the protein, compared to a normal control, the high possibility of onset of pancreatic cancer can be determined.

Because pancreatic cancer patients increase in the expression level of ABAT protein or in the expression level of mRNAs of genes encoding the proteins, and decrease in the expression level of CHI3L1 protein or in the expression level of mRNAs of genes encoding the proteins, when increase in the expression level of ABAT protein or in the expression level of mRNAs of genes encoding the protein and decrease of in the expression level of CHI3L1 protein or in the expression level of mRNAs of genes encoding the protein, compared to a normal control, the high possibility of onset of pancreatic cancer can be determined.

The expression or phrase "a subject to be examined for the onset of pancreatic cancer is higher than a normal control in terms of the protein expression level of ABAT or the mRNA expression level of a gene coding for ABAT" means that the protein expression level of ABAT protein or the mRNA expression level of a gene coding therefor in a subject to be examined for the onset of pancreatic cancer is 1.0-, 1.5-, 2-, 3-, 5-, or 10-fold higher than that in a normal control, as measured by various methods.

The expression or phrase "a subject to be examined for the onset of pancreatic cancer is lower than a normal control in terms of the protein expression level of CHI3L1 or the mRNA expression level of a gene coding for CHI3L1" means that the protein expression level of CHI3L1 protein or the mRNA expression level of a gene coding therefor in a subject to be examined for the onset of pancreatic cancer is 0.1-, 0.2-, 0.3-, 0.5- or 1-fold lower than that in a normal control, as measured by various methods.

In some embodiments, "determining that pancreatic cancer would be highly prone to occurring" may be decided according to a pancreatic cancer diagnosis formula, as exemplified by the following Formula 1.

$$f(x) = sgn\left(\sum_{i=1}^{n} \alpha_i y_i < x, x_i > + b\right)$$ [Formula 1]

wherein, x is an expression level measurement of a diagnostic marker for pancreatic cancer, $\alpha_i$ is a Lagrange multiplier in SVM, $y_i$ is a separator of normal group/pancreatic cancer group, $x_i$ is a reference measurement, and b is a correction value.

The function is derived from SVM (Support Vector Machine). SVMs are algorithms designed to estimate a function that meets a given condition on the basis of the Lagrangian optimization theory. Of them, a case when classification analysis is applied using a maximum margin classifier is called SVC (Support Vector Classification). When relative MRM measurements of ABAT and CHI3L1 are applied to the function, a function value of 1 leads to diagnosing a high likelihood of the onset of pancreatic cancer whereas a functional value of −1 accounts for a normal state.

According to the method of the present disclosure, the possibility of onset of pancreatic cancer can be readily determined on the basis of results obtained by applying protein or mRNA expression levels of ABAT and CHI3L1 to the pancreatic cancer diagnosis formula. Therefore, the determination of the possibility of onset of pancreatic cancer does not need the clinical decision of doctor.

The diagnosis function, although constructed with SVM, may be made with various types of discriminative analysis including machine learning such as Neural Network, Random Forest, etc.

In the method of the present disclosure, the protein expression levels can be measured and compared using respective antibodies specifically binding to corresponding proteins. The antibody is allowed to form an antigen-antibody complex with a corresponding protein in a biological sample, and the complex is detected.

As used herein, the term "antigen-antibody complex" means a complex in which an antigen is bound with an antibody recognizing the antigen and which is used to determine the presence or absence of a corresponding gene in a biological sample. The detection of the antigen-antibody complex can be achieved using a method well known in the art, such as a spectrometric method, a photochemical method, a biochemical method, an immunochemical method, an electrical method, a photochemical method, a chemical method, etc.

For the purpose of the present disclosure, the measurement or comparison of protein expression may be achieved using a method well known in the art, examples of which include, but are not limited to, protein chip assay, immunoassay, ligand binding assay, MALDI-TOF (Matrix Assisted Laser Desorption/Ionization Time of Flight Mass Spectrometry), SELDI-TOF (Surface Enhanced Laser Desorption/Ionization Time of Flight Mass Spectrometry), radioimmunoassay, radial immunodiffusion, Ouchterlony immunodiffusion, Rocket immunoelectrophoresis, immunohistostaining, complement fixation test, 2-D electrophoresis, liquid chromatography-mass spectrometry (LC-MS), liquid chromatography-mass spectrometry/mass spectrometry (LC-MS/MS), Western blotting, and ELISA (enzyme-linked immunosorbentassay).

In the present disclosure, LC-MRM may be used to measure and compare expression levels of ABAT and CHI3L1 proteins.

Specifically, proteins of target in a biological sample can be separated by LC using an LC analysis column while with a solution containing, by volume, 95% of distilled water, 5% of acetonitrile, and 0.1% of formic acid, and a solution containing, by volume, 5% of distilled water, 95% of acetonitrile, and 0.1% of formic acid are used with a concentration gradient from 95:5 to 15:85. Since a resolution for certain materials may vary depending on the mix ratio of the solutions, concentration gradients are set. The gradient range is optimal for separating various proteins concomitantly.

For mass analysis, MRM (multiple reaction monitoring) is performed in the MS/MS mode. SIM (Selected Ion Monitoring) takes advantage of ions formed upon collision onto an ion source of a mass spectrometer whereas MRM utilizes ions produced after specific ions are selected among from the ions broken already and then again collided against a source of a different MS in tandem. SIM is problematic in that the selected quantitative ions may interfere with quantitative analysis if they are the same as is detected in serum. On the other hand, when ions, although having the same mass, are collided once more, they are different in molecular structure from those that are not collided, exhibiting a distinct feature. Thus, the use of such ions removes the noise peaks in the background, so that MRM allows for even clearer base lines. In addition, a stable isotope standard (SIS) peptide is synthesized and measured in comparison with a target peptide, thereby enabling the accurate analysis of desired materials at the same time with higher sensitivity.

Using the above analysis methods, protein levels can be compared between a normal control and a subject suspected of the onset of pancreatic cancer, and a significant increase in the protein expression level of pancreatic cancer markers is assessed to determine the possibility of onset of pancreatic cancer.

An assay available for the measurement and comparison of mRNA expression levels of respective genes coding for ABAT and CHI3L1 proteins includes, but is not limited to, RT-PCR, competitive RT-PCR, real-time RT-PCR, RNase protection assay, Northern blotting, and DNA chip. Using the assay methods, mRNA expression levels of the pancreatic cancer markers can be measured in a subject of suspect in comparison with a normal control to diagnose or predict the onset likelihood of pancreatic cancer.

Also, the present disclosure addresses a method for providing information for diagnosis of pancreatic cancer, further comprising CA19-9 other than ABAT or CHI3L1.

Specifically, the present disclosure provides a method for diagnosing pancreatic cancer, comprising:

(a) obtaining a sample from a subject to be diagnosed for the onset of pancreatic cancer;

(b) measuring protein expression level of ABAT protein or mRNA expression level of a gene encoding ABAT protein, and protein expression level of CA19-9 or mRNA expression level of a gene encoding CA19-9 protein;

(c) comparing the expression levels of ABAT protein and CA19-9 protein or mRNA expression level of each gene encoding ABAT protein and CA19-9 protein, with those of corresponding normal control; and (d) determining that the onset or the possibility of onset of pancreatic cancer is high, when the protein expression level of ABAT protein or mRNA expression level of a gene encoding ABAT protein in the subject to be detected for onset of pancreatic cancer is higher than those of corresponding normal control, and when the expression levels of CA19-9 protein or mRNA expression level of a gene encoding CA19-9 protein in the subject to be detected for onset of pancreatic cancer is higher than those of corresponding normal control in the subject, based on the comparison result in (c) step.

Another embodiment is to provide a method for diagnosing pancreatic cancer, comprising:

(a) obtaining a sample from a subject to be diagnosed for the onset of pancreatic cancer;

(b) measuring protein expression level of ABAT, CHI3L1 and CA19-9 or mRNA expression level of each a gene encoding ABAT, CHI3L1 and CA19-9 proteins;

(c) comparing the protein expression level of ABAT, CHI3L1 and CA19-9 proteins or mRNA expression level of a gene encoding ABAT, CHI3L1 and CA19-9 proteins, with those of corresponding normal control; and (d) determining that the onset or the possibility of onset of pancreatic cancer is high, when the expression levels of ABAT protein or mRNA expression level of a gene encoding ABAT protein in the subject to be detected for onset of pancreatic cancer is higher than those of corresponding normal control, the expression levels of CHI3L1 protein or mRNA expression level of a gene encoding CHI3L1 protein in the subject to be detected for onset of pancreatic cancer is lower than those of corresponding normal control in the subject to be detected for onset of pancreatic cancer, and the expression levels of CA19-9 protein or mRNA expression level of a gene encoding CA19-9 protein in the subject to be detected for onset of pancreatic cancer is higher than those of corresponding normal control in the subject, based on the comparison result in (c) step.

An embodiment is to provide a method of detecting a maker of pancreatic cancer for providing information on diagnosis of pancreatic cancer comprising (a) obtaining a sample from a subject to be diagnosed for the onset of pancreatic cancer;

(b) measuring protein expression level of ABAT or mRNA expression level of a gene encoding the protein; and (c) comparing the protein expression level of ABAT protein or mRNA expression level of a gene encoding ABAT protein, with those of corresponding normal control.

Further embodiment is to provide a method of detecting a maker of pancreatic cancer for providing information on diagnosis of pancreatic cancer comprising (a) obtaining a sample from a subject to be diagnosed for the onset of pancreatic cancer;

(b) measuring protein expression level of each ABAT and CA19-9 or mRNA expression level of a gene encoding each protein; and (c) comparing the protein expression level of ABAT and CA19-9 proteins or mRNA expression level of a gene encoding ABAT and CA19-9 proteins, with those of corresponding normal control.

Further embodiment is to provide a method of detecting a maker of pancreatic cancer for providing information on diagnosis of pancreatic cancer comprising (a) obtaining a sample from a subject to be diagnosed for the onset of pancreatic cancer;

(b) measuring protein expression level of each ABAT and CHI3L1 or mRNA expression level of a gene encoding each protein; and (c) comparing the protein expression levels of ABAT and CHI3L1 proteins or mRNA expression level of a gene encoding each ABAT and CHI3L1 protein, with those of corresponding normal control.

Further embodiment is to provide a method of detecting a maker of pancreatic cancer for providing information on diagnosis of pancreatic cancer comprising (a) obtaining a sample from a subject to be diagnosed for the onset of pancreatic cancer;

(b) measuring protein expression level of each ABAT, CHI3L1 and CA19-9 or mRNA expression level of a gene encoding each protein; and (c) comparing the protein expression level of ABAT, CHI3L1 and CA19-9 proteins or mRNA expression level of genes encoding ABAT, CHI3L1 and CA19-9 proteins, with those of corresponding normal control.

A better understanding of the present invention may be obtained through the following examples that are set forth to illustrate, but are not to be construed as limiting the present invention.

Example 1: Excavation and Performance Analysis of Pancreatic Cancer Diagnostic Maker Over-Expressed or Under-Expressed in a Pancreatic Cancer (1) Pre-Treatment of Blood Sample To excavate the proteins over-expressed or under-expressed in a pancreatic cancer, samples were obtained from subject groups with 50 patients with PDAC, 10 patients with invasive IPMN, 22 patients with Chronic cholecystitis, or 25 normal control, as shown in Table 1. The samples from 22 patients with Chronic cholecystitis, and 25 normal control were designated as normal group, and the samples from 50 patients with PDAC and 10 patients with invasive IPMN were designated as cancer group to perform the test and analysis.

TABLE 1

| Classification | Age | | Gender | | |
| --- | --- | --- | --- | --- | --- |
| | range | Average. SD | female | male | sum |
| PDAC | 44-88 | 65.729.85 | 23 | 27 | 50 |
| Invasive IPMN | 49-81 | 63.69.66 | 4 | 6 | 10 |
| Chronic cholecystitis | 43-82 | 56.969.13 | 11 | 11 | 22 |
| Normal controls | 35-65 | 49.048.92 | 16 | 9 | 25 |

PDAC: Pancreatic ductal adenocarcinoma
IPMN: Intraductal Papillary Mucinous Neoplasm Of 40 μl of each blood sample, the most abundant 7 proteins were depleted using MARS (multiple affinity removal system) column (Agilent, USA), and the residue was concentrated through a 3 kDa filter. The concentrate was quantified by BCA. A plasma corresponding to 200 μg was taken from the concentrate, denatured with 6 M urea, and reduced and alkylated with 20 mM DTT and 50 mM iodoacetic acid. The proteins were decomposed into peptides by treatment with trypsin at a ratio of 50:1 (protein: trypsin, w/w) at 37° C. for 16 hrs, and the peptides were desalted using a C18 OASIS column (Waters, USA) and lyophilized. The lyophilizate was dissolved in solution A (98% distilled water, 2% acetonitrile, 0.1% formic acid) and added by 5 fmol of internal beta-galactosidase peptide. Then, MRM analysis was performed.

(2) Transition Selection

For MRM analysis, selection was made of a peptide that had a charge-to-mass (m/z) characteristic of a certain protein (Q1). Further, among various fragmentation ions generated from the peptide by electric collision, those with m/z characteristic of a certain protein were selected (Q3). A combination of Q1 and Q3 in which ions characteristic of a certain protein were combined was designated transition. Signals obtained by sequentially passing the characteristic ions in Q1 and Q3 through a high-resolution (triple-quadrupole) mass spectrometer were reduced into quantitative information for quantitative analysis. Using the software SKYLine developed by MacCoss's research team, University of Washington School of Medicine, Seattle, Wash., USA, up to 10 peptides per one protein were selected with regard to peptides provided with ms/ms on the basis of the peptide tandem mass spectra of the NIST (National Institute of Standards and Technology). The peptides were at least 7 amino acids to up to 24 amino acids in length.

From a total of peptides that can be produced by trypsinization, however, peptides having the following amino acids or motifs were excluded due to poor signal conditions:

(a) when methionine is present in a peptide of interest, it is prone to oxidation by ROS (reactive oxygen species) in vivo, thereby increasing the mass by 32 Da;

(b) when histidine is present in a peptide of interest, the positive charge of the R-group may alter the charge state of the peptide of interest.

(c) an N×S/T motif present in a peptide of interest may undergo N-glycosylation, resulting in a shift of mass value;

(d) when a proline residue is present just after an R or K residue in a peptide of interest, missed cleavage may occur at the R or K site, which can be cleaved by trypsin.

For a precursor charge, a peptide with a charge of +2 was selected while a charge of +1 was used as an ion charge, with a y-ion type. Distinct transitions and peptides were selected using Protein Blast P and Skyline. Finally, the transitions that fell within an expected retention time (RT) scope were used. For RT expectation, MRM analysis of 600 SIS peptides was conducted, and a calibration curve was made based on the analysis result using a hydrophobicity scale and an RT chromatogram.

(3) LC and MRM

For LC analysis, 1260-capillary LC of Agilent Technologies was employed, with a capillary RR 0.5×150 3.5 um column for peptide separation. A sample was injected in an amount of 5 μl, with a flow rate of 20 μl/min. First, the column was equilibrated with Sol A (by volume, 95% distilled water, 5% acetonitrile, 0.1% formic acid) for 10 min, after which peptides were eluted with Sol B (by volume, 5% distilled water, 95% acetonitrile, 0.1% formic acid) at a concentration gradient from 5% to 85% for 50 min and at a concentration of 85% for 5 min.

Using the mass spectrometer triple quadrupole 6490-QQQ of Agilent Technologies, transitions for the selected proteins were monitored in an MRM mode. To compensate for deviations between batches, 5 fmol beta-galactosidase peptide (GDFQFNISR (SEQ ID NO:1)[C13N15], 547.3/646.4) with which each sample was spiked was monitored simultaneously.

(4) Quantitative Analysis of Data

For quantitative analysis, the internal standard beta-galatosidase peptide (GDFQFNISR (SEQ ID NO:1) [C13N15], 547.3/646.4 m/z) was diluted to 0.09, 0.27, 0.82, 2.5, 7.4, 22.2, 66.7, and 200 fmol, and the matrix was supplemented with 10 μg of plasma as in the condition for target peptide analysis. Analysis was also done in the absence of the internal standard peptide with the aim of ascertaining endogenous signals. MRM quantification was repeated three time at all 9 concentration points to construct a standard curve.

For the result of MRM of each individual, the extract ion chromatography (XIC) of the corresponding MRM transition was produced using SKYLine (MacCoss Lab, ver1.4.1), and the peak area of each transition was calculated and plotted with time. The XIC peak area of each transition was normalized with the XIC peak area of the internal standard of beta-galatosidase peptide (GDFQFNISR (SEQ ID NO:1) [C13N15], 547.3/646.4 m/z), and on the basis of the normalization, quantitative analysis was performed for each protein.

Figure 2:
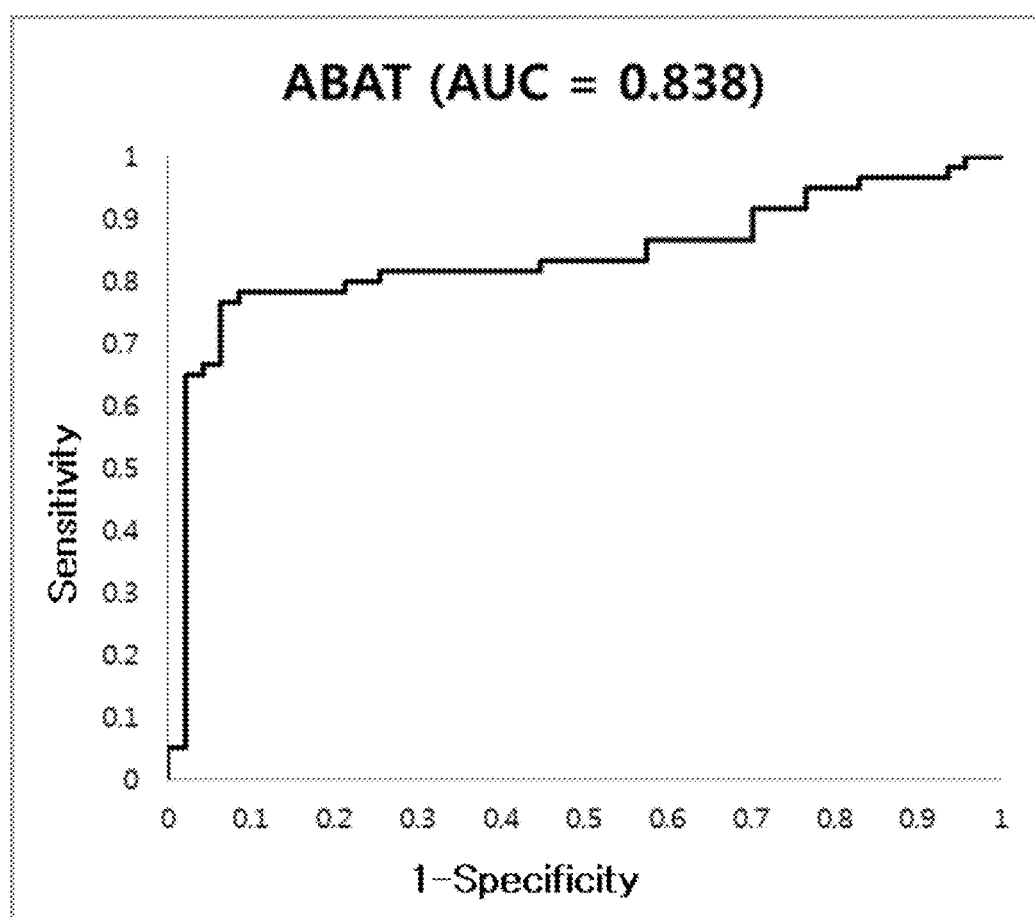
FIG. 2 is a ROC curve (Receiver Operating Characteristic) showing a diagnosis performance of cancer cell (AUC) of ABAT.

Based on the results of the MRM analysis of FIG. 1, the expression level of ABAT was significantly increased in the pancreatic cancer patient group, compared to the normal group, and thus ABAT was selected as makers for the diagnosis of pancreatic cancer. As shown in FIG. 2, the expression level of CHI3L1 was significantly decreased in the pancreatic cancer patient group, compared to the normal group, and thus CHI3L1 was selected as makers for the diagnosis of pancreatic cancer.

(5) Data Statistics

For statistical analysis, SVM (Support Vector Machine) was utilized. SVMs are algorithms designed to estimate a function that meets a given condition on the basis of the Lagrangian optimization theory. Of SVMs, a case where classification analysis is applied using a maximum margin classifier is called SVC (Support Vector Classification). In this Example, by using SVC having largest difference between two sample groups (a normal set and a pancreatic cancer set), the following pancreatic cancer diagnosis formula was constructed.

$$f(x) = sgn\left(\sum_{i=1}^{n} \alpha_i y_i <x, x_i> + b\right)$$ <Formula 1.

The formula accounts for the onset of pancreatic cancer with a calculated value of 1 and a normal state with a calculated value of −1. Decision was made of the onset or the possibility of onset of pancreatic cancer using the formula.

In detail, relative MRM measurement values of ABAT and CHI3L1 were obtained from three normal persons as follows respectively: (0.000100328 and 0.14771372), (0.000252726 and 0.260673196) and (0.000301919 and 0.190724435). When these values were applied to the formula, each obtained value were calculated to be f(0.000100328, 0.14771372)=−1, f(0.000252726, 0.260673196)=−1, and f(0.000301919, 0.190724435)=−1, indicating that the three persons were normal. Separately, relative MRM measurement values of ABAT and CHI3L1 were obtained from three pancreatic cancer patients as follows respectively: (0.037046485 & 0.023796806), (0.039893973 & 0.092394263) and (0.039590355 & 0.071735919). When these were applied to the formula, each obtained value were calculated to be f(0.037046485, 0.023796806)=1, f(0.039893973, 0.092394263)=1, f(0.039590355, 0.071735919)=1, indicating that the three persons were affected with pancreatic cancer.

When using a pancreatic cancer diagnosis formula, the diagnostic performance of a combination of ABAT and CHI3L1 for pancreatic cancer was expressed in AUC of an ROC curve. An ROC curve is expressing the change in the relationship between sensitivity and specificity on a 2D plane. A greater area under curve (AUC; 0≤AUC≤1) represents more correct information.

Figure 3:
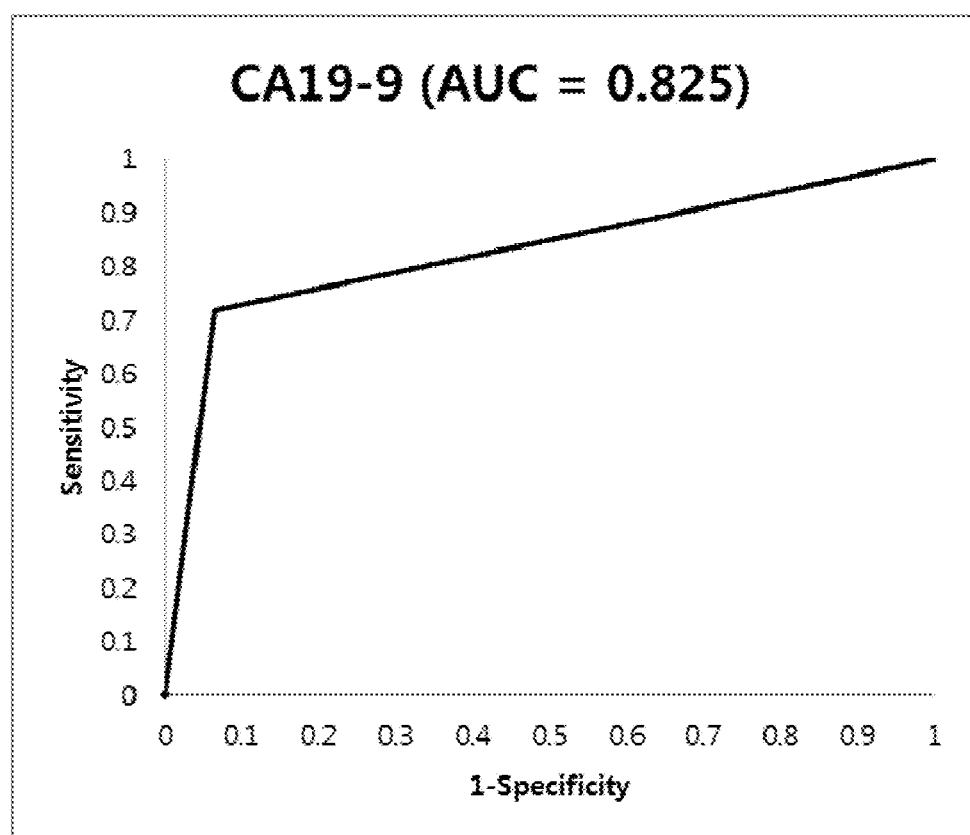
FIG. 3 is a ROC curve (Receiver Operating Characteristic) showing a diagnosis performance of cancer cell (AUC) of CA19-9 which has been known in the art as a blood marker of pancreatic cancer.
Figure 4:
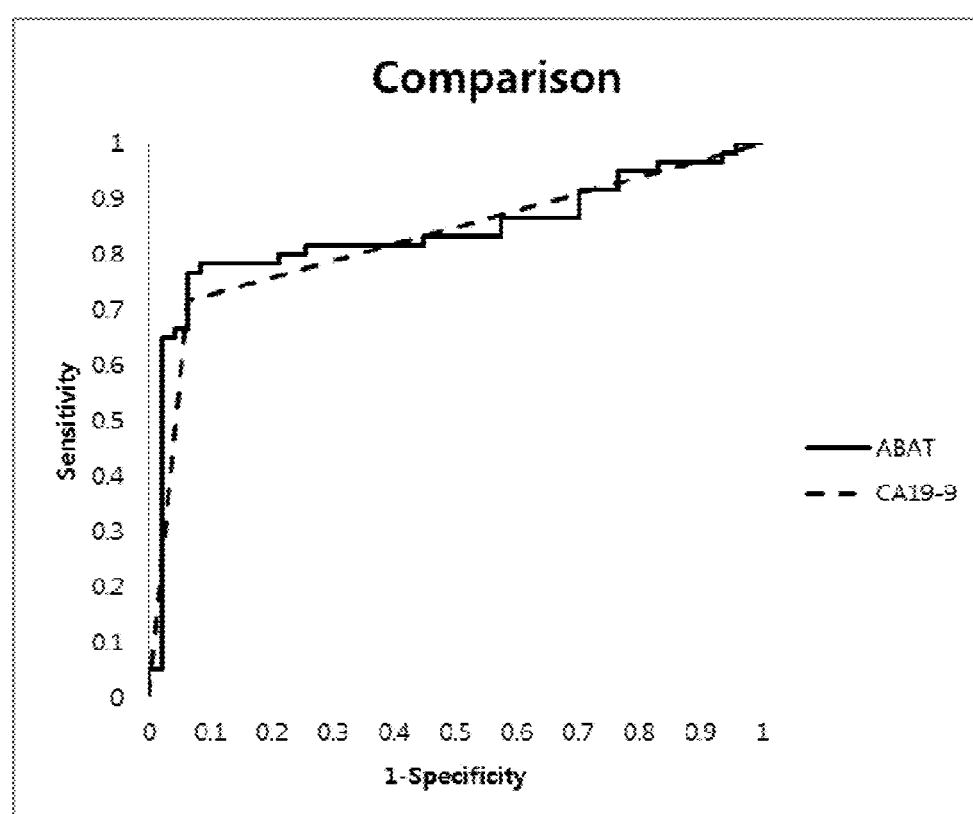
FIG. 4 is a ROC curve (Receiver Operating Characteristic) comparing the diagnosis performance of cancer cell (AUC) of ABAT, with that of CA19-9.

The combination of ABAT and CHI3L1 in accordance with the present disclosure was observed to have an AUC of 0.838, indicating that the combination exhibits excellent performance as a diagnostic marker for pancreatic cancer (FIG. 2). While CA19-9 known as commercial marker have AUC of 0.825 (FIG. 3), a combination of ABAT and CHI3L1 was observed to have higher diagnostic performance for pancreatic cancer than CA19-9 (FIG. 4).

Figure 5:
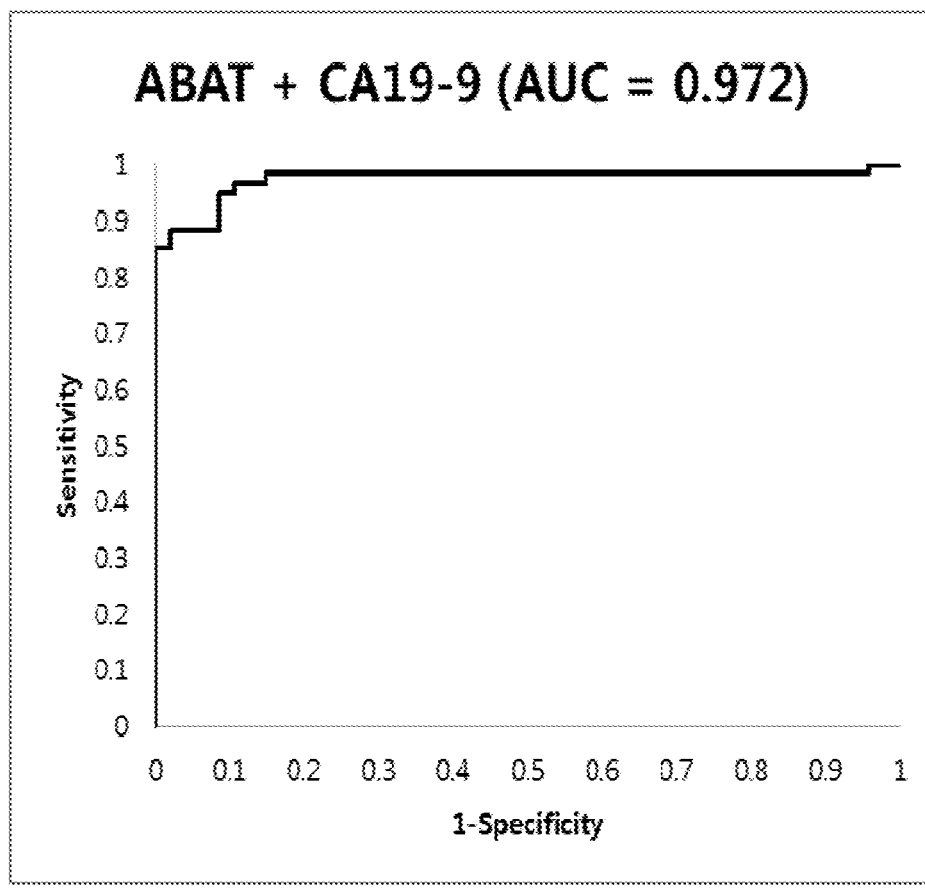
FIG. 5 is a ROC curve (Receiver Operating Characteristic) showing a diagnosis performance of cancer cell (AUC) in the combination of ABAT and CA19-9.
Figure 6:
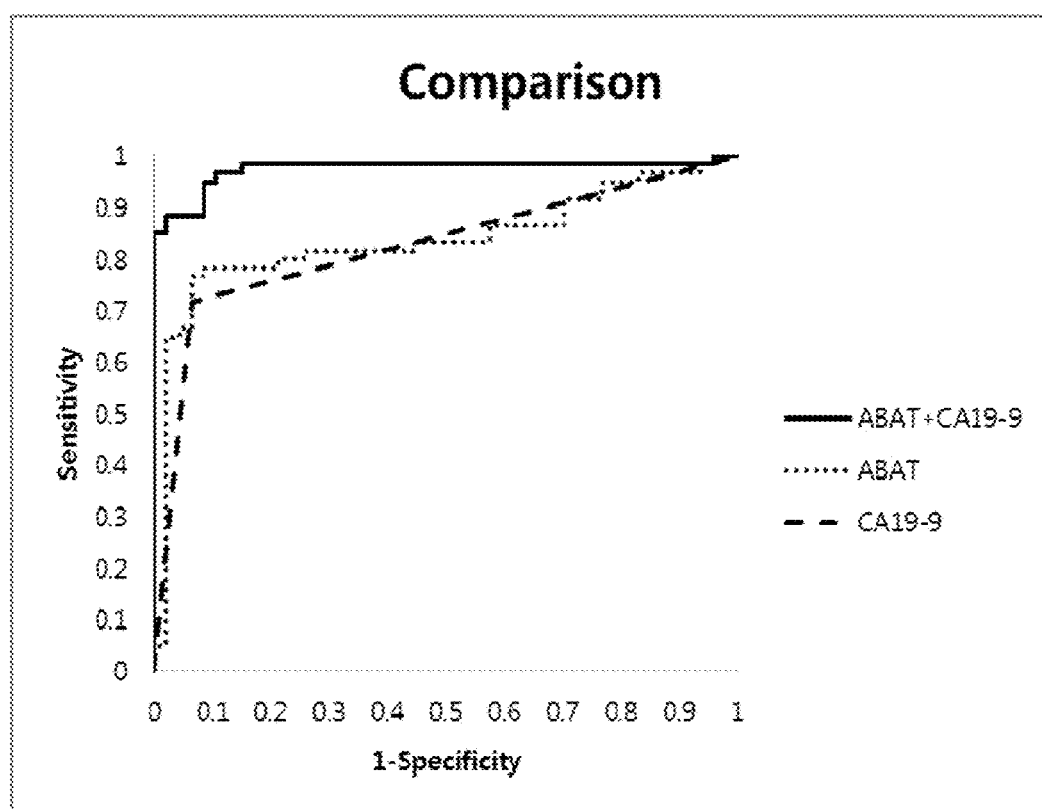
FIG. 6 is a ROC curve (Receiver Operating Characteristic) comparing the diagnosis performance of cancer cell (AUC) of CA19-9 and ABAT alone, with that of combination of CA19-9 and ABAT.

In addition, in case that ABAT, CHI3L1 and CA19-9 were used all together, AUC was 0.984 (FIG. 5), which was still higher than CA19-9 alone, or the combination ABAT and CHI3L1 (FIG. 6)

The analysis results suggest that the combination of ABAT and CHI3L1 are useful marker for detecting pancreatic cancer.

Figure 7:
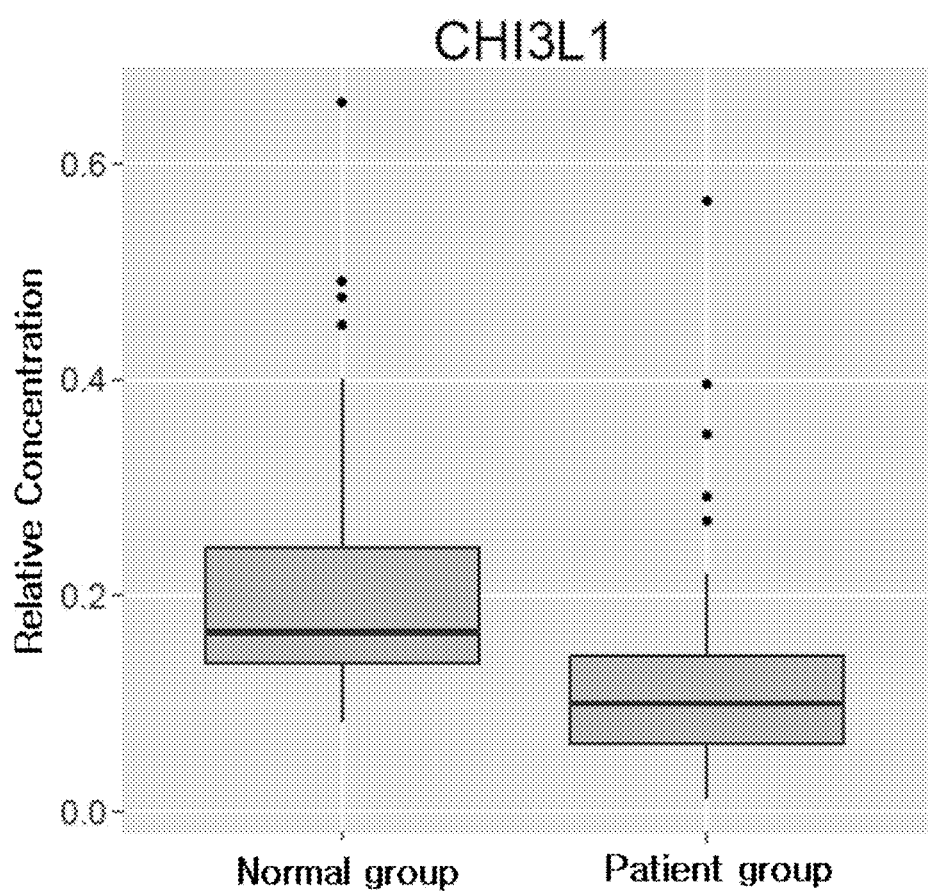
FIG. 7 is a graph showing the relative concentration of CHI3L1 protein in a control and a patient group with pancreatic cancer, as measured by MRM quantitative analysis.

Example 2: Excavation and Performance Analysis of Pancreatic Cancer Diagnostic Maker Over-Expressed or Under-Expressed in a Pancreatic Cancer According to same method of Example 1, the MRM quantitative analysis after steps of (1) to (4) showed that the expression level of CHI3L1 was significantly increased in the pancreatic cancer patient group, compared to the normal group, and thus CHI3L1 was selected as makers for the diagnosis of pancreatic cancer, as shown in FIG. 7.

(1) Data Statistics

For statistical analysis, SVM (Support Vector Machine) was utilized. SVMs are algorithms designed to estimate a function that meets a given condition on the basis of the Lagrangian optimization theory. Of SVMs, a case where classification analysis is applied using a maximum margin classifier is called SVC (Support Vector Classification). In this Example, by using SVC having largest difference between two sample groups (a normal set and a pancreatic cancer set), the following pancreatic cancer diagnosis formula was constructed.

$$f(x) = sgn\left(\sum_{i=1}^{n} \alpha_i y_i <x, x_i> + b\right)$$ <Formula 1>

The formula accounts for the onset of pancreatic cancer with a calculated value of 1 and a normal state with a calculated value of −1. Decision was made of the onset or the possibility of onset of pancreatic cancer using the formula.

In detail, relative MRM measurement values of ABAT and CHI3L1 were obtained from three normal persons as follows respectively: (0.000100328 & 0.14771372), (0.000252726 & 0.260673196) and (0.000301919 & 0.190724435). When these values were applied to the formula, each obtained value were calculated to be f (0.000100328, 0.14771372)=−1, f (0.000252726, 0.260673196)=−1, f (0.000301919, 0.190724435)=−1, indicating that the three persons were normal. Separately, relative MRM measurement values of ABAT and CHI3L1 were obtained from three pancreatic cancer patients as follows respectively: (0.037046485 & 0.023796806), (0.039893973 & 0.092394263) and (0.039590355 & 0.071735919). When these were applied to the formula, each obtained value were calculated to be f (0.037046485, 0.023796806)=1, f (0.039893973, 0.092394263)=1, f (0.039590355, 0.071735919)=1, indicating that the three persons were affected with pancreatic cancer.

When using a pancreatic cancer diagnosis formula, the diagnostic performance of a combination of ABAT and CHl3L1 for pancreatic cancer was expressed in AUC and $Snl_{Sp=0.9}$ of an ROC curve. An ROC curve is expressing the change in the relationship between sensitivity and specificity on a 2D plane. A greater area under curve (AUC; $0 \leq AUC \leq 1$) represents more correct information.

Figure 8:
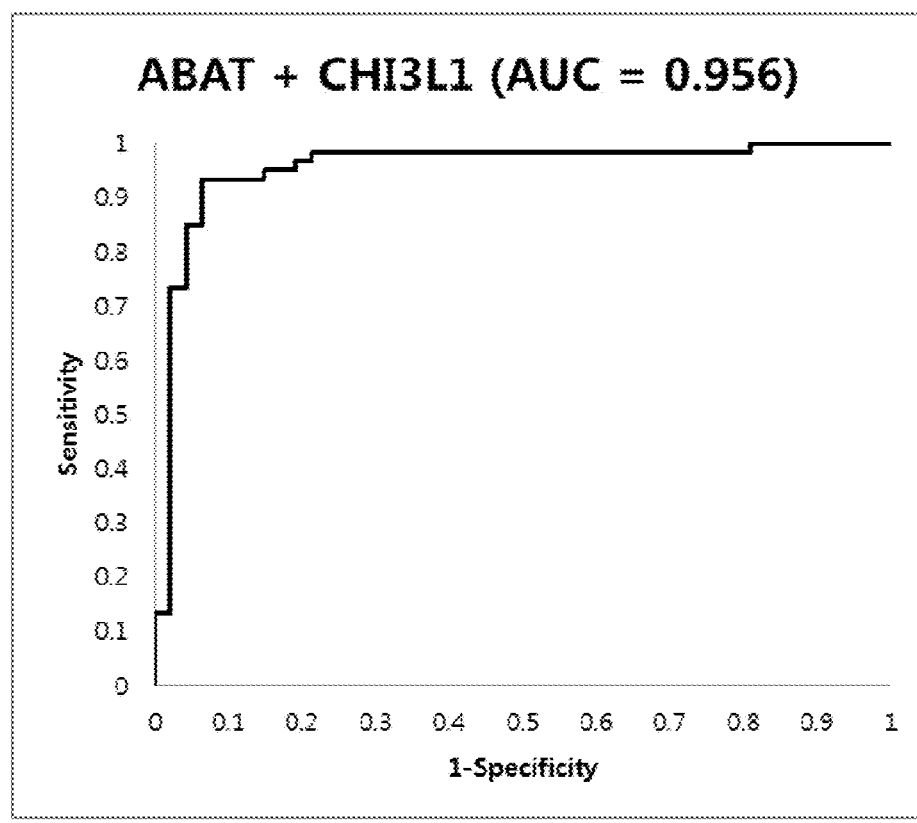
FIG. 8 is a ROC curve (Receiver Operating Characteristic) showing a diagnosis performance of cancer cell (AUC) in the combination of CHI3L1 and CA19-9.
Figure 9:
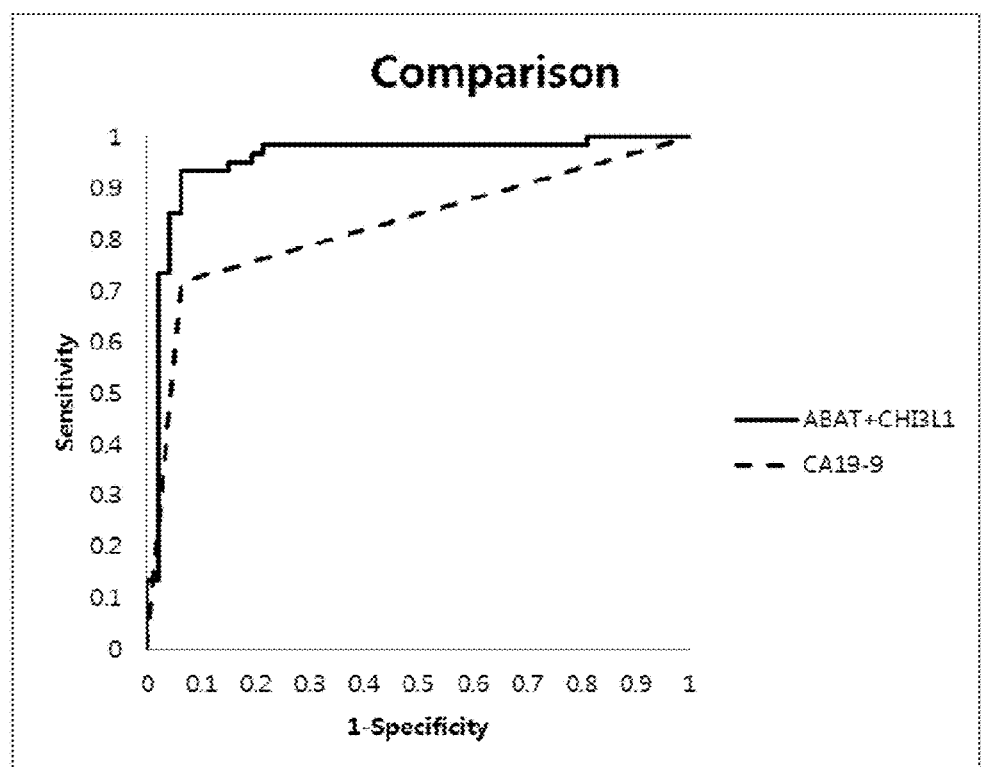
FIG. 9 is a ROC curve (Receiver Operating Characteristic) comparing the diagnosis performance of cancer cell (AUC) of CA19-9 with the combination of ABAT and CHI3L1.

The combination of ABAT and CHl3L1 in accordance with the present disclosure was observed to have an AUC of 0.956, indicating that the combination exhibits excellent performance as a diagnostic marker for pancreatic cancer (FIG. 8). While CA19-9 known as commercial marker have AUC of 0.825 (FIG. 3), a combination of ABAT and CHl3L1 was observed to have higher diagnostic performance for pancreatic cancer than CA19-9 (FIG. 9).

Figure 10:
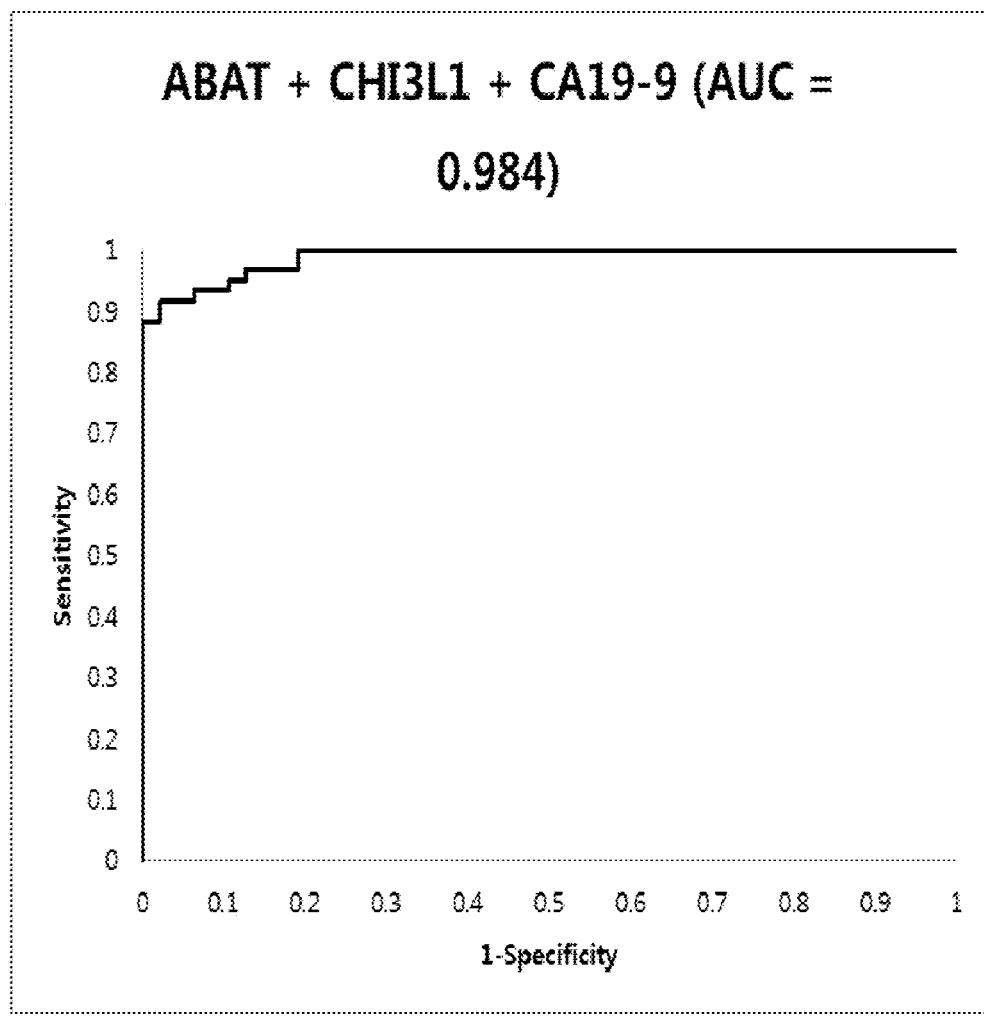
FIG. 10 is a ROC curve (Receiver Operating Characteristic) showing a diagnosis performance of cancer cell (AUC) in the combination of ABAT, CHI3L1 and CA19-9.
Figure 11:
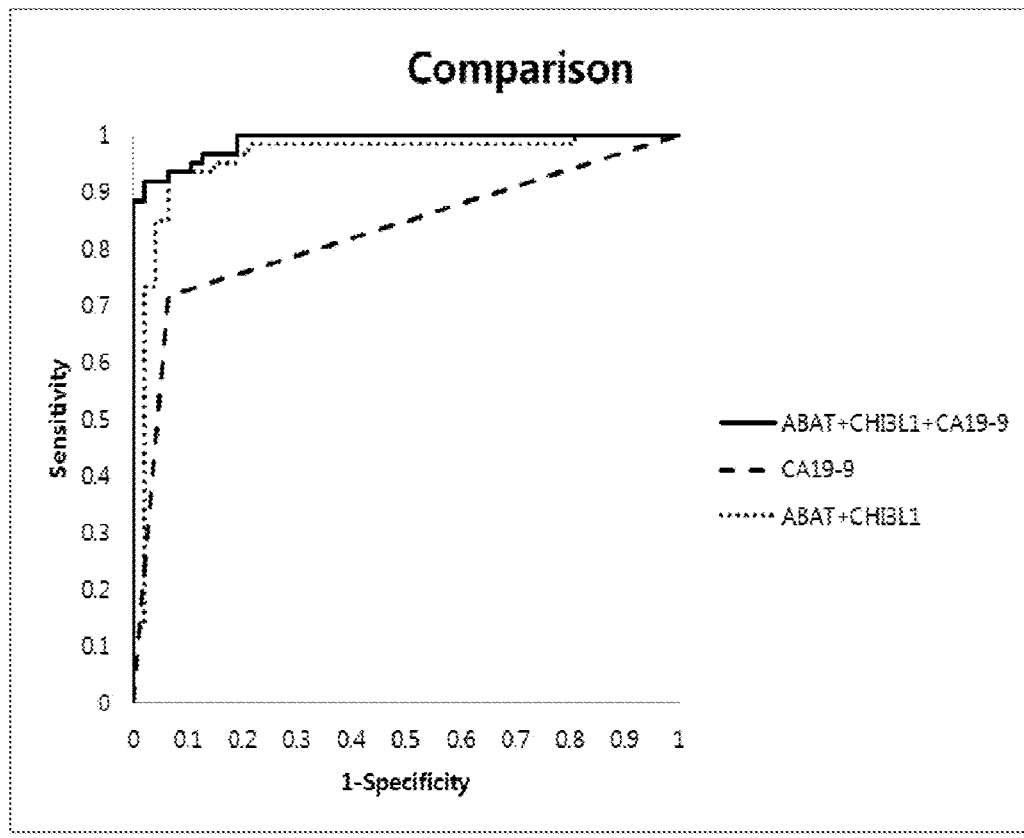
FIG. 11 is a ROC curve (Receiver Operating Characteristic) comparing a diagnosis performance of cancer cell (AUC) of combination of ABAT, CHI3L1 and CA19-9, with that of combination of ABAT and CHI3L1 or CA19-9 alone.

In addition, in case that ABAT, CHl3L1 and CA19-9 were used all together, AUC was 0.984 (FIG. 10), which was still higher than CA19-9 alone, or the combination ABAT and CHl3L1 (FIG. 11)

The analysis results suggest that the combination of ABAT and CHl3L1 are useful marker for detecting pancreatic cancer.

The invention claimed is:

1. A method for diagnosing or treating pancreatic cancer, comprising:
   (a) obtaining a sample from a subject to be diagnosed for the onset of pancreatic cancer;
   (b) measuring a protein expression level of ABAT protein (4-aminobutyrate aminotransferase) or a mRNA expression level of a gene encoding ABAT protein;
   (c) comparing the protein expression level of ABAT protein or the mRNA expression level of a gene encoding ABAT protein, with those of corresponding normal control;
   (d) determining that the possibility of onset of pancreatic cancer is high, when the protein expression level of ABAT protein or the mRNA expression level of a gene encoding ABAT protein is higher than those of corresponding normal control in the subject, based on the comparison result in (c) step; and
   (e) administering an effective amount of an anti-pancreatic cancer drug to the subject.

2. A method for diagnosing or treating pancreatic cancer, comprising:
   (a) obtaining a sample from a subject to be diagnosed for the onset of pancreatic cancer;
   (b) measuring a protein expression level of each ABAT protein (4-aminobutyrate aminotransferase) and CA19-9 protein or a mRNA expression level of each gene encoding ABAT protein and CA19-9 protein;
   (c) comparing the protein expression level of each ABAT protein and CA19-9 protein or the mRNA expression level of each gene encoding ABAT protein and CA19-9 protein, with those of corresponding normal control;
   (d) determining that the possibility of onset of pancreatic cancer is high, when the protein expression level of ABAT protein or the mRNA expression level of a gene encoding ABAT protein is higher than those of corresponding normal control in the subject, and the protein expression level of CA19-9 protein or the mRNA expression level of a gene encoding CA19-9 protein is higher than those of corresponding normal control, based on the comparison result in (c) step; and
   (e) administering an effective amount of an anti-pancreatic cancer drug to the subject.

3. A method for diagnosing or treating pancreatic cancer, comprising:
   (a) obtaining a sample from a subject to be diagnosed for the onset of pancreatic cancer;
   (b) measuring a protein expression level of ABAT (4-aminobutyrate aminotransferase) protein and CHI3LI (Chitinase-3-like protein 1 precursor) protein or a mRNA expression level of each gene encoding ABAT protein and CHI3LI protein;
   (c) comparing the protein expression level of each ABAT protein and CHI3LI protein or the mRNA expression level of each gene encoding ABAT protein and CHI3LI protein, with those of corresponding normal control;
   (d) determining that the possibility of onset of pancreatic cancer is high, when the protein expression level of ABAT protein or the mRNA expression level of a gene encoding ABAT protein is higher than those of corresponding normal control in the subject, and the protein expression level of CHI3LI protein or the mRNA expression level of a gene encoding CHI3LI protein is lower than those of corresponding normal control, based on the comparison result in (c) step; and (e) administering an effective amount of an anti-pancreatic cancer drug to the subject.

4. A method for diagnosing or treating pancreatic cancer, comprising:
(a) obtaining a sample from a subject to be diagnosed for the onset of pancreatic cancer;
(b) measuring a protein expression level of each ABAT protein, CHI3LI protein and CA19-9 protein or a mRNA expression level of each gene encoding ABAT protein, CHI3LI protein and CA19-9 protein;
(c) comparing the protein expression levels of each ABAT protein, CHI3LI protein and CA19-9 protein or a mRNA expression level of each gene encoding ABAT protein, CHI3LI protein and CA19-9 protein, with those of corresponding normal control;
(d) determining that the possibility of onset of pancreatic cancer is high, when the expression level of ABAT protein or the mRNA expression level of a gene encoding ABAT protein is higher than those of corresponding normal control in the subject,
the protein expression level of CHI3LI protein or the mRNA expression level of a gene encoding CHI3LI protein is lower than those of corresponding normal control, and
the protein expression level of CA19-9 protein or the mRNA expression level of a gene encoding CA19-9 protein is higher than those of corresponding normal control, based on the comparison result in (c) step; and (e) administering an effective amount of an anti-pancreatic cancer drug to the subject.

5. The method of claim 1, wherein the sample is blood, serum or plasma.

6. The method of claim 1, wherein the measuring of protein expression level utilizes antibodies, oligopeptides, ligands, PNAs (peptide nucleic acids), or aptamers that can specifically bind to corresponding marker proteins, respectively.

7. The method of claim 1, wherein the measuring or comparing of protein expression level is carried out by using at least one selected from the group consisting of protein chip assay, immunoassay, ligand binding assay, MALDI-TOF (Matrix Assisted Laser Desorption/Ionization Time of Flight Mass Spectrometry), SELDI-TOF (Surface Enhanced Laser Desorption/Ionization Time of Flight Mass Spectrometry), radioimmunoassay, radial immunodiffusion, Ouchterlony immunodiffusion, Rocket immunoelectrophoresis, immunohistostaining, complement fixation test, 2-D electrophoresis, liquid chromatography-mass spectrometry (LC-MS), liquid chromatography-mass spectrometry/mass spectrometry (LC-MS/MS), Western blotting, and ELISA (enzyme-linked immunosorbentassay).

8. The method of claim 1, wherein the measuring of mRNA expression level is carried out by using reverse transcription polymerase chain reaction (RT-PCR), competitive RT-PCR, real-time RT-PCR, RNase protection assay, Northern blotting, or DNA chip.

* * * * *